United States Patent [19]
Funk et al.

[11] Patent Number: 5,405,992
[45] Date of Patent: Apr. 11, 1995

[54] PROCESS FOR CONCURRENT ESTERIFICATION AND SEPARATION USING A SIMULATED MOVING BED

[75] Inventors: Gregory A. Funk, Carol Stream, Ill.; James R. Lansbarkis, Eldorado, Calif.; Ajay K. Chandhok, Mount Prospect, Ill.

[73] Assignee: UOP, Des Plaines, Ill.

[21] Appl. No.: 234,805

[22] Filed: Apr. 28, 1994

[51] Int. Cl.$^6$ .............................................. C07C 67/02
[52] U.S. Cl. ...................................... 560/265; 560/234
[58] Field of Search .................. 560/265, 234, 205; 210/659

[56] References Cited

U.S. PATENT DOCUMENTS

| | | | |
|---|---|---|---|
| 4,008,291 | 2/1977 | Zabransky et al. | 260/683.43 |
| 4,028,430 | 7/1977 | Stine et al. | 260/683.43 |
| 4,435,595 | 3/1984 | Agreda et al. | 560/234 |
| 4,777,303 | 10/1988 | Kitson et al. | 568/885 |
| 4,826,795 | 5/1989 | Kitson et al. | 502/184 |
| 5,032,523 | 7/1991 | Amano et al. | 435/280 |
| 5,126,055 | 6/1992 | Yamashita et al. | 210/659 |
| 5,149,680 | 9/1992 | Kitson et al. | 502/185 |
| 5,151,547 | 9/1992 | Sato et al. | 560/205 |

OTHER PUBLICATIONS

Vaporclyan, G. G.; Kadlec, R. H.; *AIChE Journal*, 1987, 33(8), 1334–1343.

Fish, B. B.; Carr, R. W.; *Chem. Eng. Sci.*, 1989 44, 1773–1783.

Carr, R. W.; *Preparative and Production Scale Chromatography*, Ganetsos, G. and Barker, P. E., Eds., Chromatographic Science Series, vol. 61, Marcel Decker: New York, 1003, Chapter 18, pp. 443–446–1989.

Sardin, M., Villermaux, J., *Nouv. J. Chim.*, 1979 3(4), 255–261.

Sardin, M., Schweich, D., Villermaux, J., *Preparative and Production Scale Chromatography*, Ganetsos, G., Barker, P. E., Eds., Chromatographic Science Series, vol. 61, Marcel Dekker: New York, 1993, Chap. 20, pp. 502–508.

Ray, A., Tonkovich, A. L., Aris, R., Carr, R. W., *Chem Eng. Sci.*, vol. 45. No. 8, pp. 2431–2437 (1990).

*Primary Examiner*—Arthur C. Prescott
*Attorney, Agent, or Firm*—Thomas K. McBride; Eugene I. Snyder

[57] ABSTRACT

A process for the continuous esterification of at least one alcohol and at least one carboxylic acid to form at least one ester and water, and the concurrent separation of the esterification products has been developed. The process uses a solid bed which as a catalyst for esterification and as an adsorbent for at least one of the products. The process preferably operates in the simulated moving bed mode. A specific embodiment of the invention is one where the simulated moving bed is a homogeneous mixture of at least one solid effective as an esterification catalyst and at least one solid effective as an ester or water adsorbent. Another specific embodiment is one where the simulated moving bed is a strongly acidic macroreticular polymeric resin effective both as an esterification catalyst and as an adsorbent for at least one esterification product.

14 Claims, 1 Drawing Sheet

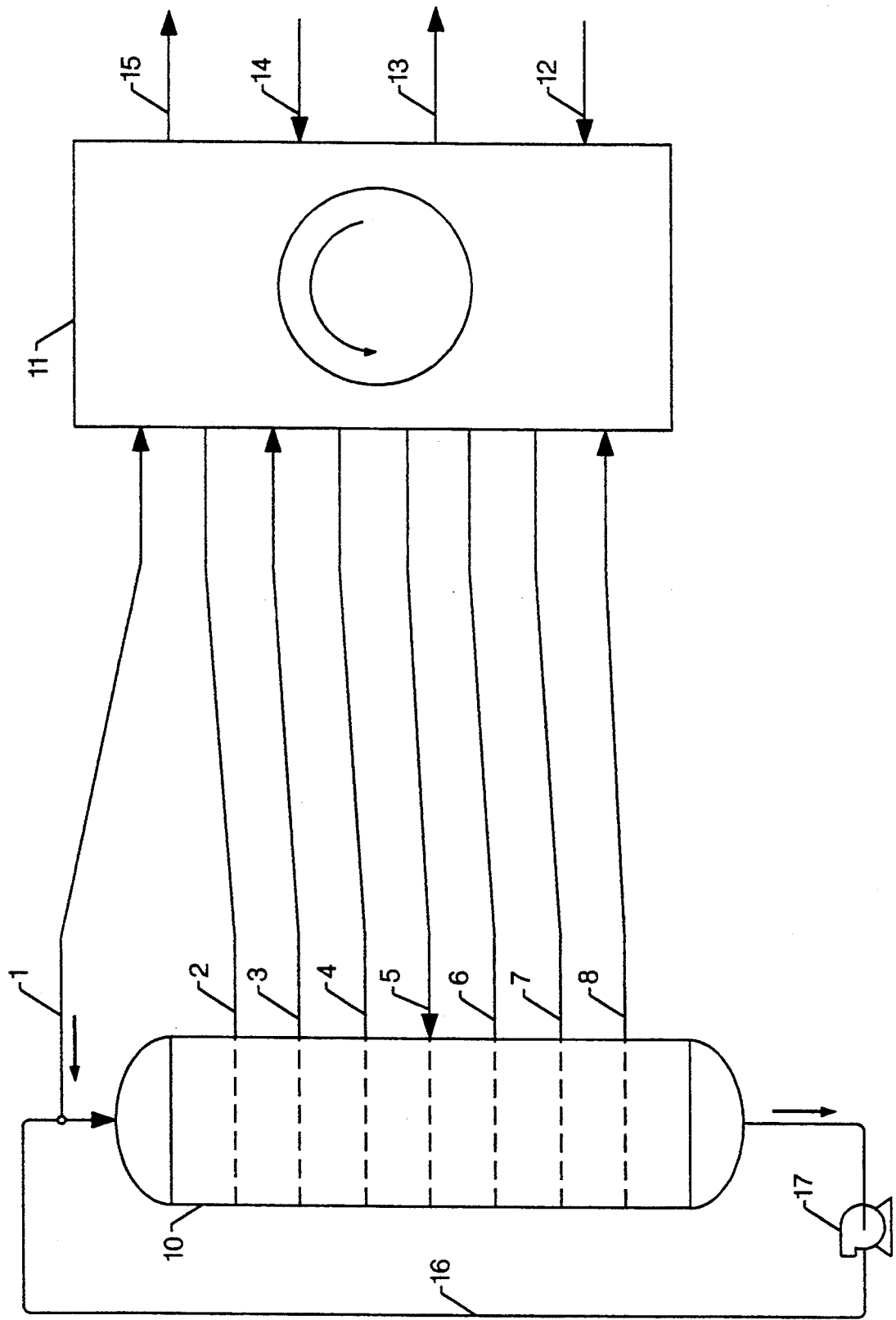

PROCESS FOR CONCURRENT ESTERIFICATION AND SEPARATION USING A SIMULATED MOVING BED

BACKGROUND OF THE INVENTION

Esters are valuable products in industry and are produced in a variety of ways. Some of the more important reactions to produce esters involve reacting (1) an acid and an alcohol, (2) an acid anhydride and an alcohol, (3) an acid chloride and an alcohol, (4) an acid and an unsaturated hydrocarbon such as an alkene or an acetylene, (5) an ester and an alcohol, (6) an ester and an add, and (7) two different esters. Esterification reactions producing esters are equilibrium limited and historical preparation techniques involved two sequential steps. The first step was the reaction step which ceased when equilibrium was reached. Generally, upon completion of the reaction, both unreacted reactants and the esterification products were all present in one mixture therefore necessitating a second step to separate the product of interest. The obvious drawbacks to the historical approach of producing esters are the cost of the two-step approach, often involving several reactors and separators, and the equilibrium-imposed limitation on the quantity of ester formed.

To overcome these drawbacks, some ester producers have used various techniques which allow the chemical reaction and the separation of the products to occur simultaneously. One such technique employed is reactive distillation. For example, U.S. Pat. No. 4,435,595 disclosed using reactive distillation to produce high purity methyl acetate from methanol and acetic acid. The reactive distillation process involved countercurrently flowing acetic acid and methanol through a single reactive distillation column in the presence of an acidic catalyst such as sulfuric acid. The acetic acid, in addition to being a reactant, also functioned as an extractive agent for the unreacted methanol and the produced water. Then the methyl acetate was separated from the acetic acid and continuously removed from the top of the column. The methanol was stripped from the water and the water was continuously removed from the bottom of the column. Using reactive distillation increased the extent of the reaction beyond equilibrium. One of the major drawbacks to this approach, however, is the cost of the reactive distillation column itseft. Since corrosive acids are used as catalysts, the column must be constructed out of materials able to withstand the harsh conditions. Such materials are generally expensive and over time will also corrode and need replacement.

Another technique which has been investigated and applied to numerous types of equilibrium-limited reactions in order to shift equilibria to favor the yield of products is the use of reactive chromatography. Reactive chromatography has been described as a technique employing a chromatographic system that is used both to convert one or more components and to simultaneously separate one or more of the products that are formed. Several different operating configurations such as a fixed bed with pressure swing or cylindrical annular bed with rotating feed input source, a countercurrent moving bed, and a countercurrent simulated moving bed have been explored. See generally, Vaporciyan, G. G.; Kadlec, R. H. *AIChE J.* 1987, 33 (8), 1334–1343; Fish, B. B.; Carr, R. W. *Chem. Eng. Sci.* 1989, 44, 1773–1783; and Cart, R. W. In *Preparative and Production Scale Chromatography*; Ganetsos, G., Barker, P. E., Eds.; Chromatographic Science Series Vol. 61; Marcel Dekker: New York, 1993; Chapter 18.

The esterification reaction of acetic acid with ethanol to form ethyl acetate and water and the simultaneous separation of the products has been accomplished in a fixed bed chromatographic reactor. See, Sardin, M.; Villermaux, J.; *Nouv. J. Chim.*, 1979, 3(4), 255–261; and Sardin, M.; Schweich, D.; Villermaux, J. In *Preparative and Production Scale Chromatography*; Ganetsos, G., Barker, P. E., Eds.; Chromatographic Science Series Vol. 61; Marcel Dekker: New York, 1993; Chapter 20, pp 502–508. In these related references, the solids contained in the fixed bed were a mixture of activated alumina to effect the separation and a cation exchange resin in acidic form to catalyze the esterification reaction. The ethyl acetate product was not adsorbed by the bed while the water product was, thereby separating the two products. The system was operated in a pulsed regime and demonstrated a conversion greater than that available at equilibrium.

Other reactions and separations, such as mesitylene hydrogenation, have been accomplished using simulated moving beds. See, Ray, A.; Tonkovich, A. L.; Aris, R.; Carr R. W. *Chem Eng. Sci.*, Vol 45 No 8 2431-2437 (1990). Some applications of simulated moving beds have focused on simultaneous reaction and catalyst regeneration. In U.S. Pat. Nos. 4,028,430 and 4,008,291 an alkylation reaction and catalyst regeneration through the removal of adsorbed water were disclosed. However, applicants are the first to realize that the simulated moving bed technique combined with reactive chromatography can be successfully applied to esterification reactions, and specifically to the esterification of an alcohol and a carboxylic acid to form an ester and water such as the esterification of methanol by acetic acid to form methyl acetate and water. Applying simulated moving bed technology to reactive chromatography for esterification will achieve high amounts of conversion with less process equipment as compared to fixed-bed systems. In addition, the disclosed invention eliminates costs associated with the recycle of unconverted reactants which are common in other processes.

SUMMARY OF THE INVENTION

The purpose of this invention is to provide a process for continuous esterification to produce at least one ester and water through contacting at least one alcohol and at least one carboxylic acid with a simulated moving bed acting as a catalyst for esterification and an adsorbent for at least one of the products, and desorbing the separated adsorbed products using a desorbent. A specific embodiment of the invention is one where the simulated moving bed is a homogeneous mixture of at least one solid effective as an esterification catalyst and at least one solid effective as an ester or water adsorbent. Another specific embodiment is one where the simulated moving bed is a strongly acidic macroreticular polymeric resin effective both as an esterification catalyst and as an adsorbent for at least one esterification product. Another yet more specific embodiment is one where the solid, effective both as a catalyst and as an adsorbent, is selected from the group consisting of Amberlyst TM -15, Amberlyst TM -18, Amberlyst TM -35 and Amberlyst TM -36. A still more specific embodiment of the invention is one where esterification is the reaction of methanol and acetic acid to form methyl acetate and water. Another more specific embodiment of the invention is one where esterification is the reaction of methanol and acetic acid to form methyl acetate and water, and the simulated moving bed is Amberlyst ™ -15.

BRIEF DESCRIPTION OF THE DRAWING

The drawing is a schematic representation of a generic commercial simulated moving catalyst and adsorbent bed process, modified and operated in accordance with the process of this invention. The drawing has been simplified by the deletion of a large number of pieces of apparatus customarily employed on a process of this nature which are not specifically required to illustrate the performance of the subject invention.

DETAILED DESCRIPTION OF THE INVENTION

The invention is a process for continuous esterification of at least two reactants to form at least one ester using a simulated moving bed to effect reactive chromatography, i.e., a process where a simulated moving bed both catalyzes the esterification reaction and effects the separation of esterification products. In general terms, the reactants, at least one alcohol and at least one carboxylic acid, are contacted with a simulated moving bed of a solid or a mixture of solids. The bed is both effective to catalyze esterification and to separate the esterification products, at least one ester and water, through adsorption of at least one product. Once separated, the adsorbed product is desorbed by a desorbent and the now separated ester and water are continuously removed from the simulated moving bed and the separated ester is recovered.

Both reactive chromatography and simulated moving bed technology are known in the art, and a general discussion of these technologies may be found in Mowry, J. R. In *Handbook of Petroleum Refining Processes*; Meyers, R. A. Ed.; McGraw-Hill: New York, 1986; pp 8–79 to 8–99 for the simulated moving bed technique; and *Preparative and Production Scale Chromatography*; Ganetsos, G., Barker, P. E., Eds.; Chromatographic Science Series Vol. 61; Marcel Dekker: New York, 1993; Chapters 16–21 for reactive chromatography. Applicants have realized that these technologies may be effectively applied to the esterification reaction of at least one alcohol and one carboxylic acid to form at least one ester and water, and the details of reactive chromatography and simulated moving bed technique as applied to the instant invention are supplied below.

The subject invention may be successfully applied to various esterification reactions where at least one alcohol and at least one carboxylic acid are reacted to form at least one ester and water. Suitable alcohols contain from one to about ten carbon atoms. Specific examples of suitable alcohols include methanol, ethanol, 1-propanol, 2-propanol, 1-butanol, 2-butanol, cyclopentanol, cyclohexanol, benzyl alcohol, 1-phenylethanol, 2-phenylethanol, 2-methyl-2-propanol, 2-methyl-1-propanol, 2-ethyl-1-hexanol, phenol, o-cresol, m-cresol, p-cresol, ethylene glycol, propylene glycol, and glycerol. Similarly, suitable carboxylic acids contain from one to about ten carbon atoms. Specific examples are formic acid, acetic acid, propionic acid, butyric acid, valeric add, caproic acid, caprylic acid, capric acid, phenylacetic acid, benzoic acid, o-toluic add, m-toluic acid, p-toluic acid and cyclohexane carboxylic acid.

Some examples of specific esterification reactions which may be performed in the present invention are: reacting methanol and acetic acid to form methyl acetate and water; reacting ethanol and acetic acid to form ethyl acetate and water; reacting propanol and acetic acid to form propyl acetate and water; reacting butanol and acetic acid to form butyl acetate and water; reacting 2-butanol and acetic acid to form 2-butyl acetate and water; reacting methanol and formic acid to form methyl formate and water; reacting ethanol and formic acid to form ethyl formate and water; reacting 2-butanol and formic acid to form 2-butyl formate and water; reacting 2-ethyl-1-hexanol and acetic acid to form 2-ethyl-1-hexyl acetate and water; reacting benzyl alcohol and acetic acid to form benzyl acetate and water; reacting methanol and propionic add to form methyl propionate and water; reacting ethanol and propionic acid to form ethyl propionate and water; reacting propanol and propionic acid to form propyl propionate and water; reacting butanol and propionic acid to form butyl propionate and water; reacting 2-pentanol and propionic acid to form 2-pentyl propionate and water; and reacting benzyl alcohol and propionic acid to form benzyl propionate and water.

Reactive chromatography requires that the desired reaction and the separation of the products are simultaneously occurring. Therefore, the simulated moving bed of the present invention must perform dual functions. The solid or mixture of solids forming the simulated moving bed must be effective as a catalyst to catalyze the esterification reaction and effective as an adsorbent which preferentially retains at least one of the esterification products in order to separate it from the other product. When the reactants enter the bed and contact the solid or mixture of solids, the esterification reaction is catalyzed and at least one ester and water is formed. The esterification reaction primarily takes place in the portion of the solid bed adjacent to and immediately downstream in the direction of the fluid flow of the introduction point of the feed, which usually contains at least one of the reactants. Since the solid or mixture of solids is also effective as an adsorbent for either the ester or water, the products begin to undergo separation immediately upon being formed. The product which is less strongly adsorbed by the adsorbent is carried with the liquid flow, and the product which is strongly adsorbed by the adsorbent is carried countercurrently with the simulated movement of the solid. The migration of the two products in opposite directions results in each product being ultimately located in different portions of the bed. Once separated, the product that was carried by the liquid flow is removed from its ultimate location by a liquid stream. Simultaneously, the product carried by the adsorbent is desorbed at its ultimate location by the introduction of a liquid desorbent and removed from the bed by a second liquid stream. The process operates continuously with the reactants being introduced, the esterification being catalyzed, and the products being separated and removed. As a consequence of the immediate separation and removal of the products, the equilibrium of the reaction is not reached and the esterification continues resulting in a greater ultimate yield of ester. Furthermore, operating costs are reduced as compared to a two-step reaction and separation process.

As previously discussed, the simulated moving bed is made up of a solid or a mixture of solids which is effective to both catalyze the esterification reaction and to separate the esterification products. There is a wide variety of solid catalysts and adsorbents available, and each esterification application may require a different solid or combination of solids. Where one solid is used, the solid must sufficiently perform both the catalyst function and the adsorbent function. For example, both the esterification of methanol and acetic acid to form methyl acetate and water and the concurrent separation of the water and methyl acetate may be sufficiently accomplished by a strongly acidic cation exchange resin such as Amberlyst TM 15, a macroreticular cation exchange polymeric resin manufactured by Rohm and Haas. Where two or more solids are used, they are used as a homogeneous mixture, and one solid may perform the catalysis function while the other performs the separation function. Examples of suitable catalysts include zeolite Beta, strongly acidic macroreticular polymeric resins and silicalite. Examples of suitable adsorbents include alumina, silica, molecular sieve carbon, activated carbon and non-strongly acidic macroreticular polymeric resins. The preferred solids are the strongly acidic macroreticular polymeric resins such as Amberlyst TM -15, Amberlyst TM -18, Amberlyst TM -35 and Amberlyst TM -36, which are capable of performing both the catalytic function and the adsorbent function. The above listed resins are manufactured by Rohm and Haas. Different esterifications and separations may require different ratios of catalyst to adsorbent or different catalyst and adsorbent combinations. Typically, the catalyst to adsorbent ratio is in the range of about 1:50 to about 50:1 with a preferred range of from about 1:10 to about 10:1.

The catalyst and adsorbent solid or mixture of solids, once chosen, is used in the process in the form of a simulated moving bed where the bed is held stationary, and the locations at which the various streams enter and leave the bed are periodically moved. The bed itself is usually a succession of fixed sub-beds, and different esterification reactions may require differing numbers of sub-beds. The most commonly used range is from about 4 sub-beds to about 24 sub-beds, with the preferred range being from 8 to 24 sub-beds. The sub-beds may be housed in one chamber or in two or more interconnected chambers. The preferred design contains one chamber.

The shift in the locations of liquid input and output streams in the direction of the fluid flow through the bed simulates the movement of the solid bed in the opposite direction. Commercially, moving the locations of liquid input and output streams is accomplished by a fluid directing device known generally as a rotary valve which works in conjunction with distributors located between the adsorbent sub-beds. The rotary valve accomplishes moving the input and output locations through first directing the liquid introduction or withdrawal lines to specific distributors located between the adsorbent sub-beds. After a specified time period, called the step time, the rotary valve advances one index and redirects the liquid inputs and outputs to the distributors immediately adjacent and downstream of the previously used distributors. Each advancement of the rotary valve to a new valve position is generally called a valve step, and the completion of all the valve steps is called a valve cycle. The step time is uniform for each valve step in a valve cycle, and the valve cycle time ranges generally from about 15 minutes to about 3 hours.

The principal liquid inputs and outputs of the simulated moving bed system consist of four streams: the desorbent, the feed, the extract, and the raffinate. Each stream flows into or out of the simulated moving bed at individual locations and at a particular flow rate which is independently controlled. The description below focuses on the situation where all the streams are liquid. It should be understood that while operating in the liquid phase is preferred, the invention could also be performed where the streams are in the gas phase.

The desorbent, which is introduced to the simulated moving bed system, contains a liquid capable of displacing a selectively adsorbed reaction product from the bed. The desorbent liquid is preferably also one of the reactants. Using a desorbent that is also one of the reactants provides for a simpler separation and recovery of the products. When the desorbent is a compound which is also a reactant, the compound may or may not be included and additionally introduced in the reactant mixture. An example of this variant is using methanol both as the desorbent and as a reactant in the esterification of acetic acid and methanol to form methyl acetate and water. While methanol is preferred as a desorbent in this reaction, an azeotrope may form between the methanol and the methyl acetate. It is contemplated that using acetic acid as the desorbent may minimize the formation of an azeotrope. Acceptable desorbents include the alcohols and carboxylic acids listed earlier. Alternatively, it is acceptable to have a solvent which is not a reactant serve as the desorbent. Of course, it is necessary that the solvent be miscible with the reactants and products, and effectively perform the desorbing function. Examples of suitable desorbents which are not reactants include diethylene glycol methyl ether and ethylene glycol dimethyl ether.

The feed, which is introduced to the simulated moving bed system, may contain at least one alcohol and/or at least one carboxylic acid which are to undergo catalytic esterification to form at least one ester and water. Typical examples of acceptable alcohols and carboxylic acids were discussed above. If the desorbent being used is also a reactant, it is not necessary for the feed to contain that same alcohol or carboxylic acid. However, when the desorbent is also an alcohol reactant, the feed must contain a carboxylic acid reactant, and when the desorbent is a carboxylic acid reactant, the feed must contain an alcohol reactant. Of course, if the desorbent being used is not a reactant, then the feed must contain at least one alcohol and at least one carboxylic acid. What is necessary is that the feed and desorbent collectively contain all required reactants.

The extract and the raffinate are both withdrawn from the simulated moving bed system. The extract contains the separated esterification product which was selectively adsorbed by the bed and then desorbed by the desorbent liquid, and the raffinate contains the other reaction product which was less strongly adsorbed by the bed. Each stream is a mixture of the respective product and desorbent. The product, if desired, may be recovered from the desorbent through conventional means such as fractionation, and the desorbent may be recycled. Each of these streams may also contain unreacted material. Although not necessary, in order to simplify recovery of the ester and to simplify the recycle of the desorbent, it is preferred that the reactants be consumed by the esterification. Similarly, in the case where the desorbent is also one of the reactants, it is preferred that the rest of the reactants be consumed by the esterification.

There also may be associated flush streams introduced to and withdrawn from the simulated moving bed and a pumparound stream. Although functionally the simulated moving bed as a whole does not have a top or a bottom, the chamber housing the bed has a physical top and bottom. The pumparound stream conducts the liquid exiting the physical bottom of the chamber back up to reenter the physical top of the chamber. In an eight sub-bed example, the pumparound stream would be the stream that conducts the effluent of sub-bed 8 from the physical bottom of the chamber to reenter sub-bed 1 at the physical top of the chamber.

Typically in a commercial system, the four principal streams are spaced strategically throughout the simulated moving bed system and divide the sub-beds into four zones, each of which performs a different function. Zone I contains the sub-beds located between the feed input and the raffinate output, and the majority of the esterification reaction and the adsorption of at least one esterification product takes place in this zone. Zone II contains the sub-beds located between the extract output and the reactant input, and some of the esterification reaction, the desorption of the less selectively adsorbed product, and the continued adsorption of the selectively adsorbed product takes place in this zone. Zone III contains the sub-beds located between the desorbent input and the extract output, and the selectively adsorbed reaction product is desorbed in this zone. The desorption may serve to regenerate the solid in addition to allowing the selectively adsorbed product to be collected. Finally, Zone IV contains the sub-beds located between the raffinate output and the desorbent input, and the purpose of this zone is to prevent the contamination or loss of the separated products.

Without intending any limitation on the scope of the present invention and as merely illustrative, this invention is explained below in specific terms as applied to one specific embodiment of the invention, the continuous esterification of acetic acid by methanol to form methyl acetate and water using Amberlyst TM -15 to effect both the catalysis of the esterification and the separation of the products. For ease of understanding, the process of the invention described below is limited to having eight sub-beds housed in one chamber. The necessary apparatus is first described and then the process of the invention as applied to the embodiment is discussed.

Referring now to the apparatus as illustrated in the drawing, distribution lines 1–8 are available to conduct liquid streams to or from the chamber 10. Chamber 10 houses eight sub-beds of Amberlyst TM -15. The distribution lines connect with the simulated moving bed at locations between successive sub-beds and separate the simulated moving bed into four zones as described earlier. The distribution lines 1–8 are also connected to a rotary valve 11. Rotary valve 11 is further connected to line 12 which conducts the feed, a 1:1 molar mixture of methanol and acetic acid, to the valve, line 13 which conducts raffinate, methyl acetate diluted in methanol, away from the valve, line 14 which conducts desorbent, methanol, to the valve, and line 15 which conducts extract, water diluted in methanol, away from the valve. Each of the lines 12–15 is provided with a flow rate sensor and flow control valve (not shown). Line 16 conducts the effluent, or pumparound stream, from the bottom of chamber 10 back to the top of chamber 10 and is equipped with a pump 17.

Using the described apparatus, the invention is performed as follows. The flow rates of each of the lines 12–15 and the step time of rotary valve 11 may be first set to selected values based on the operator's experience. The starting position of the rotary valve is not important; for this illustration the starting position of the rotary valve is such that the desorbent is directed to chamber 10 through distribution line 1, the extract is directed from chamber 10 through distribution line 3, the feed is directed to chamber 10 through distribution line 5, and the raffinate is directed from chamber 10 through distribution line 8. When the step time has elapsed, rotary valve 11 advances one index and now directs the desorbent through distribution line 2, the extract through distribution line 4, the feed through distribution line 6, and the raffinate through distribution line 1. When the step time has again elapsed, the streams will again be directed to the next successive distribution line in the direction of the flow, and the continued progression of the streams will simulate the movement of the solid bed in the countercurrent direction.

For ease of understanding, the operation is described with rotary valve 11 in the starting position as above. When the feed containing the reactants, conducted in distribution line 5, enter the simulated moving bed chamber 10 and contact the Amberlyst TM -15, the esterification reaction is catalyzed, and methyl acetate and water are formed. The acetic acid and some methanol is consumed. The methyl acetate, which is weakly absorbed by the Amberlyst TM -15, is carried with the fluid flow and withdrawn from the bed in the raffinate stream conducted in distribution line 8. The water, which is absorbed by the Amberlyst TM -15, is carried with the solid bed in its countercurrent simulated movement thereby being separated from the methyl acetate. The water is desorbed from the Amberlyst TM -15 by the desorbent methanol and conducted to the bed through distribution line 1. The water is withdrawn from the simulated moving bed chamber 10 in the extract stream conducted in distribution line 3. Since the raffinate and the extract both contain methanol, each stream is treated downstream in a fractionator (not shown) to remove and recycle the methanol. Since an azeotrope is formed between the methyl acetate and the methanol, further treatment such as extractive distillation may be required.

It must be emphasized that the above description is merely illustrative of a preferred embodiment and is not intended as an undue limitation on the generally broad scope of the invention. Moreover, while the description is narrow in scope, one skilled in the art will understand how to extrapolate to the broader scope of the invention. For example, operation of the invention where the sub-beds of the simulated moving bed may be housed in two or more interconnected chambers can be readily extrapolated from the foregoing description. Similarly, one skilled in the art would understand that the simulated moving bed may also be a homogeneous mixture of two or more solids, or that the desorbent and the feed may have different compositions. Furthermore, the optimum number of sub-beds, the optimum cycle time, and the optimum flow rates would be readily determined by one skilled in the art.

What is claimed is:

1. A process for continuous esterification with concurrent separation of the esterification products comprising:

a. continuously introducing a desorbent and a feed, which collectively comprise at least one alcohol and at least one carboxylic add, to a simulated moving bed of a solid or a mixture of solids effective to catalyze esterification and to separate esterification products by selective adsorption of at least one product;

b. reacting the alcohol and the carboxylic acid to form the esterification products consisting of at least one ester and water;

c. separating the ester from the water by selectively adsorbing at least one product on the solid or mixture of solids;

d. desorbing the selectively adsorbed product from the solid or mixture of solids using the desorbent;

e. collecting the separated ester and water; and f. recovering the separated ester.

2. The process of claim 1 where the alcohol contains from 1 to about 10 carbon atoms.

3. The process of claim 1 where the alcohol is selected from the group consisting of methanol, ethanol, 1-propanol, 2-propanol, 1-butanol, 2-butanol, cyclopentanol, cyclohexanol, benzyl alcohol, 1-phenylethanol, 2-phenylethanol, 2-methyl-2-propanol, 2-methyl-1-propanol, 2-ethyl-1-hexanol, phenol, o-cresol, m-cresol, p-cresol, ethylene glycol, propylene glycol, and glycerol.

4. The process of claim 1 where the carboxylic acid contains from 1 to about 10 carbon atoms.

5. The process of claim 1 where the carboxylic acid is selected from the group consisting of formic acid, acetic acid, propionic acid, butyric acid, valeric acid, caproic acid, caprylic acid, capric acid, phenylacetic acid, benzoic acid, o-toluic acid, m-toluic acid, p-toluic acid and cyclohexene carboxylic acid.

6. The process of claim 1 where the ester is selected from the group consisting of methyl acetate, ethyl acetate, propyl acetate, butyl acetate, 2-butyl acetate, methyl formate, ethyl formate, 2-butyl formate, 2-ethyl-1-hexyl acetate, benzyl acetate, methyl propionate, ethyl propionate, propyl propionate, butyl propionate, 2-pentyl propionate and benzyl propionate.

7. The process of claim 1 where the simulated moving bed is a mixture of solids containing a solid effective as an esterification catalyst selected from the group consisting of zeolite Beta, strongly acidic macroreticular polymeric resins and silicalite.

8. The process of claim 1 where the simulated moving bed is a mixture of solids containing a solid effective as an adsorbent selected from the group consisting of alumina, silica, molecular sieve carbon, activated carbon and non-strongly acidic resins.

9. The process of claim 1 where the simulated moving bed is a mixture of solids containing a solid effective as an esterification catalyst and a solid effective as an adsorbent present in a ratio of from about 1:50 to about 50:1.

10. The process of claim 1 where the simulated moving bed is a mixture of solids containing a solid effective as an esterification catalyst and a solid effective as an adsorbent present in a ratio of from about 1:10 to about 10:1.

11. The process of claim 1 where the simulated moving bed is a strongly acidic macroreticular polymeric resin which is effective as a catalyst and effective as an adsorbent.

12. The process of claim 11 where the strongly acidic macroreticular polymeric resin is selected from the group consisting of Amberlyst TM-15, Amberlyst TM-18, Amberlyst TM-35 and Amberlyst TM-36.

13. The process of claim 1 where the alcohol is methanol, the carboxylic acid is acetic acid, and the ester is methyl acetate.

14. The process of claim 13 where the solid effective as a catalyst and the solid effective as an ester or water adsorbent is Amberlyst TM-15.

* * * * *

UNITED STATES PATENT AND TRADEMARK OFFICE
CERTIFICATE OF CORRECTION

PATENT NO. : 5,405,992
DATED : April 11, 1995
INVENTOR(S) : Gregory A. Funk et al It is certified that error appears in the above-indentified patent and that said Letters Patent is hereby corrected as shown below:

In Column 9, line 3: change "add" to --acid--.

Signed and Sealed this

Twenty-seventh Day of June, 1995

Attest:

BRUCE LEHMAN

Attesting Officer

Commissioner of Patents and Trademarks